United States Patent [19]

Adams et al.

[11] Patent Number: 4,800,228
[45] Date of Patent: Jan. 24, 1989

[54] 4,7-DIACETOXY-2-(4-METHOXYBENZYL)-3,5,6-TRIMETHYLBENZOFURAN

[75] Inventors: Julian Adams, Westmount; Yvan Guindon, Montreal, both of Canada

[73] Assignee: Merck Frosst Canada, Inc., Quebec, Canada

[21] Appl. No.: 64,269

[22] Filed: Jun. 18, 1987

[51] Int. Cl.$^4$ .......................................... C07D 307/86
[52] U.S. Cl. .................................... 549/470; 546/196; 548/525; 549/362; 549/398; 549/435; 549/466; 549/467; 549/469
[58] Field of Search ............... 549/362, 398, 435, 466, 549/467, 470; 546/196; 548/525; 514/320, 422, 452, 456, 464, 469, 470

[56] References Cited

U.S. PATENT DOCUMENTS 4,663,347  5/1987  Atkinson et al. ................... 549/466

OTHER PUBLICATIONS

Wagner et al., Synthetic Org. Chemistry, Wiley & Sons Inc., pp. 154–155 and 481–483 (1953).

Primary Examiner—Mary C. Lee
Assistant Examiner—Bernard I. Dentz
Attorney, Agent, or Firm—Gabriel Lopez; Hesna J. Pfeiffer

[57] ABSTRACT

4,7-Diacyloxybenzofuran derivatives of Formula I, are disclosed. These compounds are useful as inhibitors of mammalian leukotriene biosynthesis. As such, these compounds are useful therapeutic agents for treating allergic conditions, asthma, cardiovascular disorders, inflammation, psoriasis and allergic conjunctivitis. The compounds are also useful as analgesics and as cytoprotective agents.

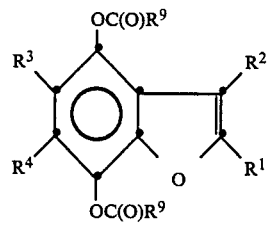

1 Claim, No Drawings

4,7-DIACETOXY-2-(4-METHOXYBENZYL)-3,5,6-TRIMETHYLBENZOFURAN

CROSS-REFERENCE

The 4,7-benzofurandiones described herein are the subject of a patent application entitled "4,7-BENZOFURANDIONE DERIVATIVES", filed on even date herewith, Ser. No. 064,152.

BACKGROUND OF THE INVENTION

This invention involves certain 4,7-diacyloxybenzofuran derivatives. These compounds are useful as inhibitors of mammalian leukotriene biosynthesis. As such, these compounds are useful therapeutic agents for treating allergic conditions, asthma, cardiovascular disorders, and inflammation. The compounds are also useful as analgesics and as cytoprotective agents.

The leukotrienes are a novel group of biologically active mediators derived from arachidonic acid through the action of lipoxygenase enzyme systems. There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biologically active material known as the slow reacting substance of anaphylaxis.

The leukotrienes are potent smooth muscle contracting agents, particularly on respiratory smooth muscle but also on other tissues (e.g., gall bladder). In addition, they promote mucous production, modulate vascular permeability changes, and are potent inflammatory agents in human skin. The most important compound in the second group of leukotrienes is Leukotriene $B_4$, a dihydroxy fatty acid. This compound is a potent chemotactic agent for neutrophils and eosinophils and, in addition, may modulate a number of other functions of these cells. It also affects other cell types such as lymphocytes and, for example, may modulate the action of T-suppressor cells and natural killer cells When injected in vivo, in addition to promoting the accumulation of leukocytes, Leukotriene $B_4$ is also a potent hyperalgesic agent and can modulate vascular permeability changes through a neutrophil dependent mechanism. Both groups of leukotrienes are formed following oxygenation of arachidonic acid through the action of a 5-lipoxygenase enzyme. See for example, D. M. Bailey et al., *Ann. Rpts. Med. Chem.* 17 203 (1982).

The leukotrienes are potent spasmogens of human trachea, bronchus and lung parenchymal strips, and when administered to normal volunteers as aerosols are 3,800 times more potent that histamine at inducing a 50% decrease in air flow at 30% of vital capacity. They mediate increases in vascular permeability in animals and promote mucous production in human bronchial explants. In addition, Leukotriene $B_4$ may also mediate mucous production and could be an important mediator of neutrophil and eosinophil accumulation in asthmatic lungs 5-lipoxygenase products are also thought to be regulators of mast cell degranulation and recent studies with human lung mast cells have suggested that 5-lipoxygenase inhibitors, but not corticosteroids, may suppress antigen-induced mast cell degranulation. In vitro studies have shown that antigen challenge of human lung results in the release of leukotrienes and in addition purified human mast cells can produce substantial amount of leukotrienes. There is therefore good evidence that leukotrienes are important mediators of human asthma. 5-lipoxygenase inhibitors would therefore be a new class of drugs for the treatment of asthma. See for example, B. Samuelsson, *Science* 220, 568–575 (1983).

Psoriasis is a human skin disease which affects between two and six percent of the population. There is no adequate therapy for psoriasis and related skin conditions. The evidence for leukotriene involvement in these diseases is as follows. One of the earliest events in the development of prepapillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured as well as large amounts of lipoxygenase products. Leukotriene $B_4$ has been detected in psoriatic lesions, but not in uninvolved skin, in biologically significant amounts.

Leukotrienes can be measured in nasal washings from patients with allergic rhinitis and are greatly elevated following antigen challenge. Leukotrienes may mediate this disease through their ability to regulate mast cell degranulation, by modulating mucous production and mucocillary clearance and by mediating the accumulation of inflammatory leukocytes Leukotrienes can also mediate other diseases. These include atopic dermatitis, gouty arthritis, and gall bladder spasms. In addition, 62ey may have a role in cardiovascular disease because leukotrienes $C_4$ and $D_4$ act as coronary and cerebral arterial vasoconstrictors and these compounds may also have negative inotropic effects on the myocardium. In addition, the leukotrienes are important mediators of inflammatory diseases through their ability to modulate leukocyte and lymphocyte function.

SUMMARY OF THE INVENTION

It has now been discovered that certain substituted diacyloxybenzofurans of Formula I are effective inhibitors of leukotriene biosynthesis. Thus, these compounds are useful therapeutic agents for treating allergic conditions, asthma, cardiovascular disorders such as angina, inflammation, for amelioration of skin diseases like soriasis and atopic eczema, for treatment of allergic conjunctivitis, as analgesics, and as cytoprotective agents.

DETAILED DESCRIPTION OF THE INVENTION

The compounds of the present invention are compounds of the formula:

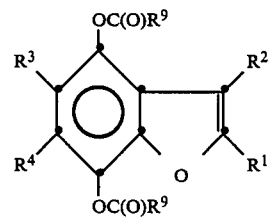

I $R^1$ is

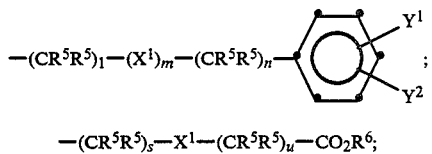

$-(CR^5R^5)_s-X^1-(CR^5R^5)_u-CO_2R^6;$ or z lower alkyl;

$R^2$ is lower alkyl;

$R^3$ and $R^4$ is each independently $R^2$, Cl, $X^2R^2$, or $X^3R^5$;

$R^5$ is H or lower alkyl, or two $R^5$'s when attached to N may be joined to form a 5- or 6-membered ring;

$R^6$ is H or lower alkyl;

$R^7$ is H or lower alkyl;

$R^8$ is H or lower alkyl;

$R^9$ is H or lower alkyl;

$X^1$ is $X^2$ or $X^3$;

$X^2$ is S, S(O), S(O)$_2$;

$X^3$ is O or $NR^5$;

$X^4$ is $X^2$ or $X^3$ $Y^1$ and $Y^2$ is each independently: H, $R^2$, $X^2R^2$, $X^3R^5$, halogen, $(X^4)_w$-$(CR^5R^5)_z$-$CO_2R^7$, $CF_3$, $COR^8$, $CONR^5R^5$, or $S(O_2)NR^5R^5$; or $Y^1$ and $Y^2$ may be joined to form a 5- or 6-membered ring, containing one or two O atoms, such as —OCH$_2$O, —OCH$_2$CH$_2$O—, —OCH$_2$CH$_2$—, or —OCH$_2$CH$_2$—;

l and n is each independently 0 to 5;

m is 0 or 1;

s is 0 to 3;

u is 0 to 3 provided that when $R^6$ is H, then u is 1 to 3;

w is 0 or 1; and z is 0 to 3, provided that when w is 1 and $R^7$ is H, then z is 1 to 3;

and the pharmaceutically acceptable salts thereof.

Compounds of this invention are represented in Table 1.

straight, branched, or cyclic configuration. Examples of "lower alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like.

It is intended that the definitions of any substituent (e.g., $R^5$, $X^2$, $X^3$, etc.) in a particular molecule is independent of its definitions elsewhere in the molecule. Thus, $CR^5R^5$ represents CH(CH$_3$), CH$_2$, C(CH$_3$)$_2$, etc.

Abbreviations used throughout are as follows:

Me is methyl,

Et is ethyl, n-Pr is normal propyl, t-Bu is tertiary butyl,

Ac is acetyl, $C_6H_3Y^1Y^2$ is

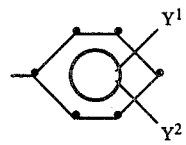

In those instances when asymmetric centers are present, more than one stereoisomer is possible, and all possible isomeric forms are deemed to be included within the planar structural representations shown. Optically active (R) and (S) isomers may be resolved using conventional techniques known to the skilled artisan.

The term "pharmaceutically acceptable salts" refers to salts prepared from pharmaceutically acceptable non-toxic bases, including organic and inorganic bases, and from pharmaceutically acceptable non-toxic acids, including organic and inorganic acids.

When the compound of the present invention is

TABLE 1

NOVEL 4,7-DIACYLOXYBENZOFURANS

| Ex. | $R^1$ | $Y^1$ | $Y^2$ | $R^3$ | $R^4$ | $R^9$ |
|---|---|---|---|---|---|---|
| 1 | $CH_2C_6H_3Y^1Y^2$ | 4-OMe | H | Me | Me | Me |
| 2 | $CH_2C_6H_3Y^1Y^2$ | 3-Cl | 4-OMe | n-Pr | Cl | Me |
| 3 | $CH_2C_6H_3Y^1Y^2$ | 4-OMe | H | n-Pr | Me | Me |
| 4 | $CH_2C_6H_3Y^1Y^2$ | 4-OMe | H | n-Pr | SEt | Me |
| 5 | $CH_2C_6H_3Y^1Y^2$ | 4-OMe | H | n-Pr | S(O)Et | Me |
| 6 | $CH_2C_6H_3Y^1Y^2$ | 4-OMe | H | n-Pr | S(O)$_2$Et | Me |
| 7 | $CH_2C_6H_3Y^1Y^2$ | 4-OMe | H | Me | n-Pr | Me |
| 8 | Et | — | — | Me | Me | Me |
| 9 | $CH_2C_6H_3Y^1Y^2$ | 3,4-OCH$_2$O | H | Me | Me | Me |
| 10 | $(CH_2)C_6H_3Y^1Y^2$ | 4-OMe | H | Me | Me | Me |
| 11 | $CH(CH_3)C_6H_3Y^1Y^2$ | 4-OMe | H | Me | Me | Me |
| 12 | $SC_6H_3Y^1Y^2$ | H | H | Me | Me | Me |
| 13 | $SCH_2CO_2Me$ | — | — | Me | Me | Me |
| 14 | $C_6H_3Y^1Y^2$ | H | H | Me | Me | Me |
| 15 | $C_6H_3Y^1Y^2$ | 4-OAc | H | Me | Me | Me |
| 16 | $C_6H_3Y^1Y^2$ | 4-OMe | H | Me | Me | t-Bu |
| 17 | Et | — | — | Me | Me | n-Pr |
| 18 | $C_6H_3Y^1Y^2$ | 4-OMe | H | Me | Me | H |

As used herein, "halogen" is F, Cl, Br, or I.

As used herein, the term "lower alkyl" includes those alkyl groups of from 1 to 7 carbon atoms of either a acidic, pharmaceutically acceptable salts may be prepared from the appropriate base. Salts derived from inorganic bases include aluminum, ammonium, calcium, copper, ferric, ferrous, lithium, magnesium, manganic, manganous, potassium, sodium, zinc salts, and the like.

are represented in Table 2. Certain di- and trisubstituted 4,7-benzofurandiones which are also useful intermediates are represented in Table 3 as Formula Ib, wherein $R^1$ and $R^3$ are as defined in Formula I.

TABLE 2
TETRA-SUBSTITUTED 4,7-BENZOFURANDIONES

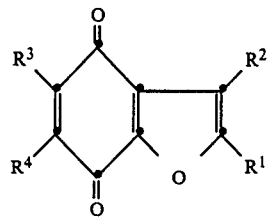

Ia

| Prep. No. | $R^1$ | $Y^1$ | $Y^2$ | $R^2$ | $R^3$ | $R^4$ |
|---|---|---|---|---|---|---|
| 1. | CO$_2$Et | — | — | Me | Cl | Cl |
| 2. | CO$_2$Et | — | — | Me | Me | Me |
| 3. | CH$_2$C$_6$H$_3$Y$^1$Y$^2$ | 4-OMe | H | Me | Me | Me |
| 4. | CO$_2$Et | — | — | Me | n-Pr | OMe |
| 5. | CO$_2$Et | — | — | Me | n-Pr | Cl |
| 6. | CO$_2$Et | — | — | Me | n-Pr | SEt |
| 7. | CO$_2$Et | — | — | Me | n-Pr | S(O)Et |
| 8. | CO$_2$Et | — | — | Me | n-Pr | S(O)$_2$Et |
| 9. | CH$_2$C$_6$H$_3$Y$^1$Y$^2$ | 3-Cl | 4-OMe | Me | n-Pr | Cl |
| 10. | CH$_2$C$_6$H$_3$Y$^1$Y$^2$ | 4-OMe | H | Me | n-Pr | Me |
| 11. | CH$_2$C$_6$H$_3$Y$^1$Y$^2$ | 4-OMe | H | Me | n-Pr | SEt |
| 12. | CH$_2$C$_6$H$_3$Y$^1$Y$^2$ | 4-OMe | H | Me | n-Pr | S(O)Et |
| 13. | CH$_2$C$_6$H$_3$Y$^1$Y$^2$ | 4-OMe | H | Me | n-Pr | S(O)$_2$Et |
| 14. | CH$_2$C$_6$H$_3$Y$^1$Y$^2$ | 4-OMe | H | Me | n-Pr | NH$_2$ |
| 15. | CH$_2$C$_6$H$_3$Y$^1$Y$^2$ | 4-OMe | H | Me | Me | n-Pr |
| 16. | CH$_2$C$_6$H$_3$Y$^1$Y$^2$ | 4-OH | H | Me | Me | Me |
| 17. | Et | — | — | Me | Me | Me |
| 18. | CH$_2$C$_6$H$_3$Y$^1$Y$^2$ | 3,4-OCH$_2$O | — | Me | Me | Me |
| 19. | (CH$_2$)$_2$—C$_6$H$_3$Y$^1$Y$^2$ | 4-OMe | H | Me | Me | Me |
| 20. | CH(CH$_3$)C$_6$H$_3$Y$^1$Y$^2$ | 4-OMe | H | Me | Me | Me |
| 21. | SC$_6$H$_3$Y$^1$Y$^2$ | H | H | Me | Me | Me |
| 22. | SCH$_2$CO$_2$Me | — | — | Me | Me | Me |
| 23. | SCH$_2$CO$_2$H | — | — | Me | Me | Me |
| 24. | C$_6$H$_3$Y$^1$Y$^2$ | H | H | Me | Me | Me |

Particularly preferred are the ammonium, calcium, magnesium, potassium and sodium salts. Salts derived from organic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, pharmaceutically acceptable salts may be prepared from the appropriate acid. Such acids include acetic, benzensulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, panoic, pantothenic, phosphoric, succinic, sulfuric, tataric acid, p-toluenesulfonic, and the like. Particularly preferred are citric, hydrobromic, hydrochloric maleic, phosphoric, sulfuric, and tartaric acids.

The tetra-substituted 4,7-benzofurandiones of Formula Ia, wherein $R^1$, $R^2$, $R^3$ and $R^4$ are defined as in Formula I, are useful as intermediates for the preparation of the Formula I compounds. These compounds

TABLE 3

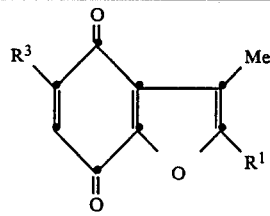

Ib

| Prep. No. | $R^1$ | $Y^1$ | $Y^2$ | $R^3$ |
|---|---|---|---|---|
| 25 | CO$_2$Et | — | — | H |
| 26 | CO$_2$Et | — | — | n-Pr |
| 27 | H | — | — | n-Pr |
| 28 | CH$_2$C$_6$H$_3$Y$^1$Y$^2$ | 4-OMe | H | n-Pr |
| 29 | CH$_2$C$_6$H$_3$Y$^1$Y$^2$ | 4-OH | H | n-Pr |
| 30 | CH$_2$C$_6$H$_3$Y$^1$Y$^2$ | 4-OMe | H | H |
| 31 | CH$_2$CO$_2$Et | — | — | n-Pr |

The compounds of Formula I may be prepared by reducing a compound of Formula Ia with a suitable reducing agent such as sodium dithionite, zinc, or hydrogen and then acylating with an acid anhydride or an acyl halide of structure (R$^9$C(O))$_2$O, R$^9$C(O)Cl, or R$^9$C(O)Br, wherein R$^9$ is H or lower alkyl.

The following reaction schemes illustrate the preparation of compounds of the present invention:

SCHEME I

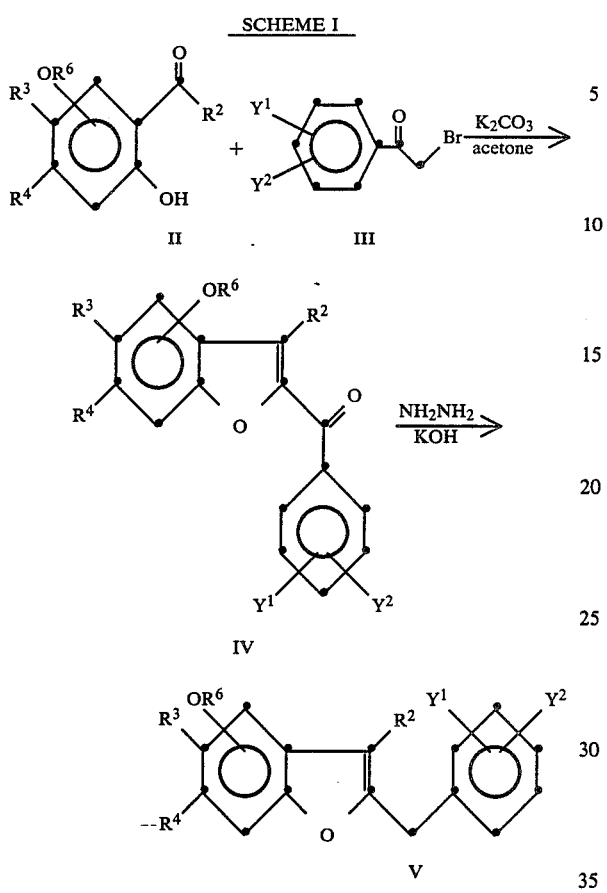

a suitable acetophenone (II) is reacted with a substituted phenacyl bromide (III) at a temperature ranging from room temperature to about 150° C. in an inert solvent (preferably at reflux in acetone) in the presence of a base (for example, an alkali metal hydroxide or carbonate) to give the corresponding benzoyl benzofuran derivative (IV). The compound of the formula IV is then reduced to give V. For example, subsequent treatment of IV with hydrazine and a strong base at a temperature of about 150° to 210° C. preferably using the Huang Minlon modification of Wolff-Kishner conditions (J. Am. Chem. Soc. 68, 2487 (1946)) yields the desired benzyl benzofuran derivative V. Alternatively, compound IV can be reduced to compound V using zinc amalgam and a strong acid (preferably hydrochloric acid). See, for example, Ber. 46, 1837 (1913). Alternatively, compound IV can be reduced to compound V using a mixture of lithium aluminum hydride and aluminum chloride in ether or tetrahydrofuran as solvent at a temperature range varying from 0° C. to 65° C.

SCHEME II

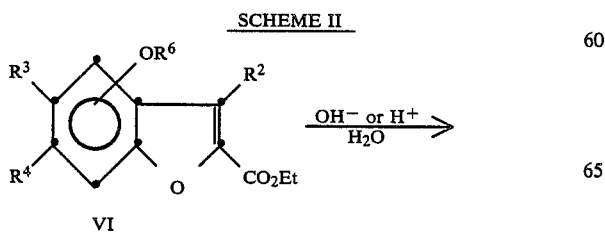

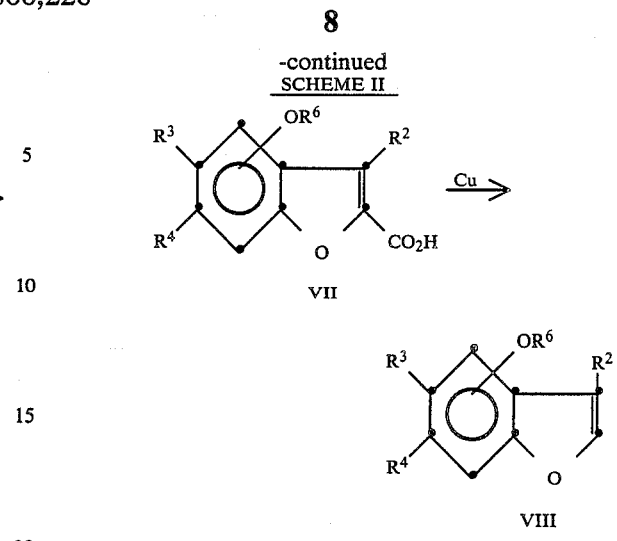

According to the method of Scheme II, hydrolysis of an appropriate compound of the formula VI with a strong acid or a strong base in water, or a mixture of water and an organic water soluble solvent, such as methanol, ethanol, tetrahydrofuran, etc. at a temperature ranging from room temperature to reflux (preferably, reflux) yields the corresponding acid of formula VII. Compounds of the formula VI are disclosed in EP No. 146,243, published June 26, 1985. The acid of formula VII is then decarboxylated to yield the corresponding benzofuran derivative of the formula VIII. This may be done by heating the acid in quinoline in the presence of copper. It can also be done by heating at reflux compound VII with a strong acid such as hydrochloric acid in a two-phase system made up of toluene and aqueous acid. Benzene or xylene or other aromatic hydrocarbons can be substituted for toluene.

SCHEME III

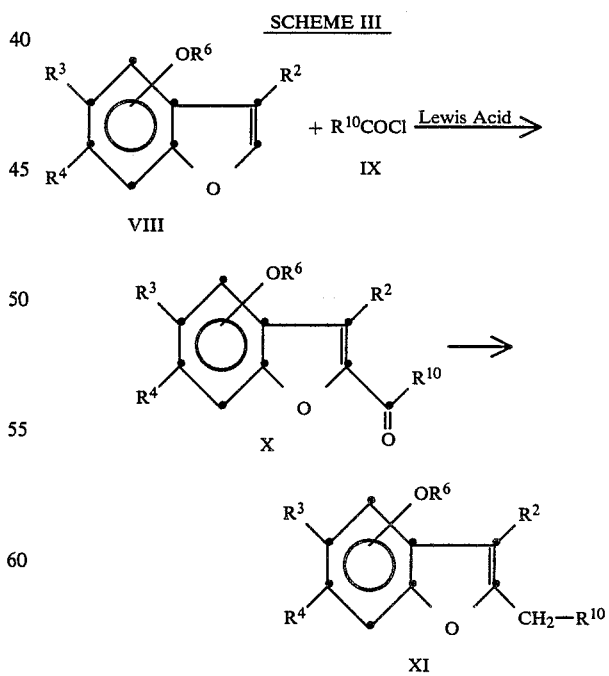

$R^{10}$ is loweralkyl or $C_6H_3Y^1Y^2$.

Following Scheme III, Compound VIII, which is unsubstituted in position 2, can be reacted with an acid halide IX in the presence of a Lewis acid, preferably aluminum chloride, to yield the 2-acyl derivative X. This reaction is best carried out in a solvent such as methylene chloride or ethylene dichloride at a temperature ranging from 0° to 25° C. The compound of the Formula X is then reduced to give the compound of Formula XI. For example, subsequent treatment of X with hydrazine and a strong base at a temperature of about 150° to 210° C. using the Huang-Minlon modification of Wolff-Kishner conditions (J. Am. Chem. Soc. 68, 2487 (1946)) yields the 1 desired alkyl benzofuran derivative XI. Alternatively, compound X can be reduced to compound XI using zinc amalgam and a strong acid (preferably hydrochloric-acid). See, for example, Ber., 46. 1837 (1913).

Alternatively, compound X can be reduced to compound XI using a mixture of lithium aluminum hydride and aluminum chloride in ether or tetrahydrofuran as solvent at a temperature range varying from 0° to 65° C.

SCHEME IV

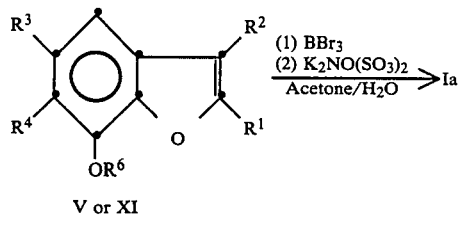

An alternative method to prepare ester VI of Scheme II is shown in Scheme IV. The substituted phenol may be 0-alkylated with a suitable bromomester and cyclized using concentrated $H_2SO_4$ to form benzofuran ester VI.

SCHEME V

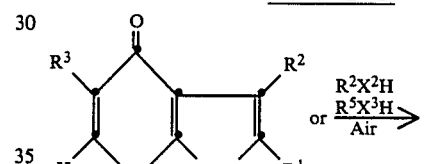

-continued
SCHEME V

V or XI

Oxidation of a phenol V or XI to its corresponding 4,7-benzofuandione Ia is conveniently ahcieved using Fremy,s salt ($K_2NO(SO_3)_2$) in acetone/water at 50? C. An alternative oxidative method employs a catalytic amount of bis(salicylidene)ethylenediiminecobalt (II) (salcomine) (see Parker, Tet. Lett., 22 397–400(1981)) or related catalysts described in Frostin-Rio, J. Chem. Soc. Perkin Trans. I, 1971 (1984), dissolved in a suitable solvent such as dimethylformamide (DMF), with stirring in the presence of air.

When $R^6$ is V or XI is lower alkyl, the compond is first converted to the corresponding phenol (R=H) by treatment with $BBr^3$.

SCHEME VI

XIV

Ic

Substitution of the 4,7-benzofurandione XIV by $R^2X^2$ or $R^5X^3$ can be achieved by oxidative addition by a 1,4 conjugate Michael type reaction in the presence of air as illustrated in Scheme VI, wherein $R^{11}$ is $R^2X^2$ or $R^5X^3$.

SCHEME VII

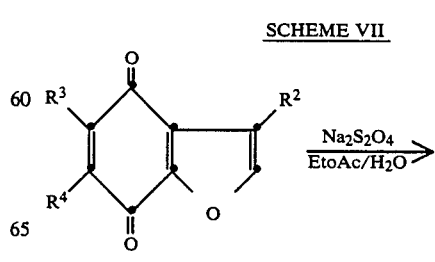

XV

-continued
SCHEME VII

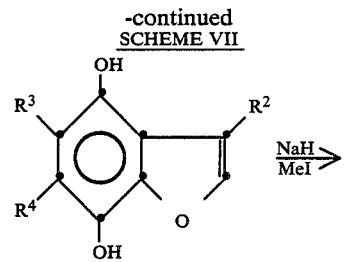

XVI

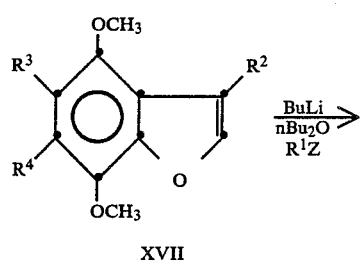

XVII

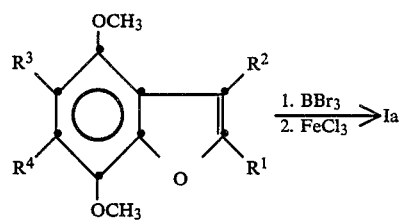

XVIII

Z is a leaving group such as a sulfide, halogen, tosylate, or mesylate.

Substitution at the 2-position of the 4,7-benzofurandione XV may be achieved following Scheme VII. Reductive methylation produces benzofuran XVII, which can be lithiated at the 2-position and reacted with suitable elecltrophiles. The dimethoxy benzofuran XVIII can be demthylated and re-oxidized to give the tetrasubstituted 4,7-benzofurandione Ia.

SCHEME VIII

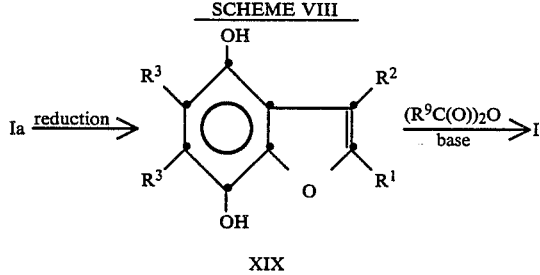

XIX

The compounds I of the present invention are prepared as indicated in Scheme VIII. In a first step, the 4,7-benzofurandiones Ia are reduced with a suitable reducing agent to the 4,7-benzofurandiols, XIX, which are then acylated to obtain the compounds of Formula I. The diols may be isolated and characterized if desired, but it is usually more convenient to acylate the crude XIX after a minimum of purification. Particularly useful as a reducing agent is sodium dithionite ($Na_2S_2O_4$) in a two-phase system of water and an organic solvent such as ethyl acetate, diethyl ether or methylene chloride. Another suitable reducing agent is zinc in acetic acid or an acid anhydride. In the latter system (acid anhydride), the acylated product I is obtained directly from the reaction. Another method of reduction of compound Ia to the diols XIX is by treatment with hydrogen and a suitable catalyst such as platinum, palladium or rhodium in a solvent such as ethanol, ethyl acetate, acetic acid, toluene or the like. If the solvent contains (or is entirely) an acid anhydride, the diacyloxybenzofurans I may be obtained directly.

Acylation of the diols XIX is conveniently carried out using an acid anhydride in pyridine, optionally containing a catalytic amount of a strong organic base such as 4-dimethylaminopyridine. Other convenient acylating agents are acyl chlorides or acyl bromides, and when $R^9$ is H, formic acetic anhydride may be used. Suitable organic bases other than pyridine include quinoline, triethylamine, diisopropylethylamine, and the like. Inorganic bases such as $NaHCO_3$, $Na_2CO_3$, $K_2CO_3$ and the like, suspended in non-reactive solvents such as diethyl ether, ethyl acetate, acetone and the like may also be used.

The compounds of Formula I may be tested using one or more of the following assays to determine their mammalian leukotriene biosynthesis inhibiting activity and other relevant activities.

RBL-1 5-Lipoxygenase

Rat basophilic leukemia (RBL-1) cells are sonicated and centrifuged at 125000 xg. The resulting supernatant fraction is incubated with arachidonic acid (labelled with $^{14}C$) to convert a portion of it to $^{14}C$-5(S)-hydroxyicosatetraenoic acid (5-HETE). Compounds being evaluated as inhibitors of 5-Lipoxygenase are added prior to the addition of arachidonic acid. 5-HETE is isolated by extraction and paper chromatography, and quantitated by determining the amount of radioactivity (cpm) associated with 5-HETE.

Reference: Egan, R. W.; Tischler, A. M.; Baptista, E. H.; Ham, E. A.; Soderman, D. D.; and Gale, P. H.; *Advances in Prostaglandin, Thromboxane and Leukotriene Research*, 11, 151, (1983), (Samuelsson, B.; Ramwell, P.W.; and Paoletti, R.; (eds.), Raven Press, N.Y.

Mouse Macrophase Assay

Mouse peritoneal macrophages are treated sequentially with arachidonic acid (labelled with tritium); the compound being evaluated as an inhibitor, and a stimulator (zymosan). Metabolites derived from arachidonic acid ($PGE_2$, 6-keto $PG-F_{1a}$ and leukotriene $C_4$) are separated from the incubation medium by extraction and chromatography, and then quantitated by determining the amount of radioactivity (cpm) associated with each of them. Inhibitors cause a reduction in the amount of radioactivity (cpm) associated with a given metabolite. (This protocol is identical to that described in the reference except that the radioactivity herein associated with the $LTC_4$ is determined by counting an aliquot of the final aqueous solution directly rather than chromatographing it first.

Reference: Humes, J. L. et al., *J. Biol. Chem.*, 257, 1591-4, (1982).

Rat Polymorphonuclear Leukocyte (P.M.N.) Assay

Rats under ether anesthesia are injected (intraperitoneally) with 8 ml of a suspension of sodium caseinate (6 grams in about 50 ml water). After 15 to 24 hours the rats are sacrificed ($CO_2$) and the cells from the peritoneal cavity are recovered by lavage with 20 ml of buffer (Eagles Minimal Essential Medium containing 30 mM HERPES adjusted to pH 7.4 with NaOH). The cells are pelleted (350×g, 5 min.), resuspended in buffer with vigorous shaking, filtered through lens paper, recentrifuged and finally suspended in buffer at a concentration of 10 cells/ml. A 500 μl aliquot of the suspension (PMN) and test compound are preincubated for 2 minutes at 37° C, followed by the addition of 10 μM A-23187 calcium ionophore (Calbiochem). The suspension is stirred for an additional 4 minutes then bioassayed for $LTB_4$ content by adding an aliquot to a second 500 μl portion of the PMN at 37° C. The $LTB_4$ produced in the first incubation causes aggregation of the second PMN, is measured as a change in light transmission. The size of the assay aliquot is chosen to give a submaximal transmission change (usually −70%) for the untreated control. The percentage inhibition of $LTB_4$ formation is calculated from the ratio of transmission change in the sample to the transmission change in the compound-free control.

Antigen Challenge 'in vitro' Assay

Male guinea pigs weighing 300–350 g are sensitized by injecting (intraperitoneally) 0.5 ml of a suspension containing 0.4 mg of egg albumin (Ovalbumin, Grade V, Sigma Chemical Co.) and 4.0 g aluminum hydroxide in 19.6 ml of saline. Two weeks are permitted for sensitization to occur.

Three sensitized guinea pigs are stunned and exanguinated. The tracheas are removed, freed of adhering tissue and divided longitudinally by cutting through the cartilaginous tissue directly opposite the muscle insertion. Each opened trachea is then transected between every second cartilage. Four of the cut sections are tied together, end to end, in a series with No.7 silk thread ensuring that the tracheal muscles are all in the same vertical plane. Thus, each chain consists of tissue from three different animals.

The chain so formed is then suspended under 1 g of tension (by silk ties at each end) in a 20 ml organ bath containing 10 ml of modified[1] Krebs-Henseleit buffer solution gassed with 95% $O_2$ and 5% $CO_2$ at 37° C. Mepyramine (0.55 μg/ml) and indomethacin (2.67 μg/ml) are added to the buffer to avoid the contribution of histamine receptors and cyclooxygenase products to the contraction. To record responses one end of the tracheal chain is attached to a Gould-Statham UC-2 force displacement transducer which is connected to a Beckman Type R-dynograph. The preparations are allowed to equilibrate for one hour during which time the tissues are automatically washed (10 ml volume displacement) every 6 minutes.

[1]modified Krebs solution in grams/liter and (mM):
NaCl—6.87 (120); glucose—2.1 (11); $NaHCO_3$—2.1 (25); KCl—0.32 (4.72); $CaCl_2$—0.28 (2.5);
$MgSO_4.7H_2O$—0.11 (0.5); $KH_2PO_4$—0.16 (1.2); pH at bathing solution =7.35±0.05.

After the equilibration period the tissues are primed with methacholine (3 μg/ml; 1.5×10⁻⁵M), washed and allowed to recover to baseline. The tissues are treated again with a second dose of methacholine, washed, allowed to return to baseline and washed for an additional hour.

Two chains are used as a control. These are incubated in a concentration of egg albumin sufficient to induce an average contraction of 50–80% of the methacholine response.

Each compound to be tested is added to two other baths (at a final concentration in each bath of 10 μg/ml) 15 minutes prior to challenging the fresh chains with egg albumin.

The response of the challenged tissue is expressed as a percentage of the methacholine maximum. The percentage inhibition for each compound is then calculated. Compounds which at 10 μg/ml (final concentration) inhibit the egg albumin response by 50% or more are retested at a lower concentration.

Asthmatic Rat Assay

Rats are obtained from an inbred line of asthmatic rats. Both female and male rats from 200 to 300 g are used.

Egg albumin (EA), grade V, crystallized and lyophilized, is obtained from Sigma Chemical Co., St. Louis. *Bordetella pertussis* vaccine, containing 30×10⁹ killed bacteria per ml is obtained from the Institute Armand-Frappier, Laval des Rapides, Quebec. Aluminum hydroxide is obtained from the Regis Chemical Company, Chicago.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No. 0000 pneumotachograph is inserted into one end of the box and coupled to a Grass volumetriC pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 ml of a 3% solution of antigen in saline is placed into each nebulizer and the aerosol is generated with air from a small Potter diaphragm pump operating at 10 psi and a flow 8 liters/minute.

Rats are sensitized by injecting (subcutaneously) 1 ml of a suspension containing 1 mg EA and 200 mg aluminum hydroxide in saline. Simultaneously, they receive an injection (intraperitoneally) of 0.5 ml of *B. pertussis* vaccine. They are used between days 14 and 18 postsensitization. In order to eliminate the serotonin component of the response, rats are pretreated intravenously 5 minutes prior to aerosol challenge with 30 gm/kg methylserzide. Rats are then exposed to an aerosol of 3% EA in saline for exactly 1 minute, then their respiratory profiles are recorded for a further 25 to 30 minutes. The duration of continuous dyspnoea is measured from the respiratory recordings.

Compounds are generally administered either intraperitoneally 1 hour prior to challenge or orally 1 and ½ hours prior to challenge. They are either dissolved in dimethylsulfoxide or suspended in 0.1% methocel and 0.5% Tween 80. The volume injected is 2 ml/kg (intraperitoneally) or 10 ml/kg (orally). Prior to oral treatment rats are starved overnight. Their activity is determined in terms of their ability to decrease the duration of symptoms of dyspnoea in comparison with a group of vehicle-treated controls. Usually, a compound is evaluated at a series of doses and an $ED_{50}$ is determined. This is defined as the dose (mg/kg) which would inhibit the duration of symptoms by 50%.

PAF-Induced Hyperalgesia Assay

Female Sprague-Dawley rats, 35 to 40 g are fasted overnight. Platelet activating factor, PAF, (L-lecithin B-acetyl O-alkyl) 1 μg/0.1 ml is given by subplantar injection in the rat paw. The compounds to be evaluated are homogenized in Aqueous Vehicle (0.9% benzyl alcohol, 0.5% Tween 80 and 0.4% methylcellulose) and administered orally in a volume of 0.1 ml, 30 minutes prior to PAF.

Animals are tested 1, 2, 3 and 4 hours after PAF administration. The vocalization threshold, defined as the pressure (mmHg) needed to evoke a squeak response, was recorded for both the injected and contralateral paw. No animal is subjected to pressure greater than 60 mmHg. Hyperalgesia is defined as a decrease in vocalization threshold as compared to a normal paw. Percent inhibition of hyperalgesia is calculated as the proportion of animals with vocalization thresholds greater than 200% of controls.

Brewer's Yeast Hyperalgesia Assay

The standard method [Winter, C. A. et al., *J. Pharm. Exo. Ther.* 150, 165–171 (1965)] for yeast hyperalgesia is used. Female Sprague-Dawley rates, 35–40 g are fasted overnight. A 5% solution (volume 0.1 ml) of Brewer's yeast is injected into the rat paw. The compound is homogenized in aqueous vehicle and given orally 2 hours after yeast. Vocalization thresholds are recorded 1 hour after drug (3 hours after yeast). Percent inhibition of hyperalgesia is vocalization thresholds greater than 25 mmHg.

The compounds of the Formula I have unexpected activity as inhibitors of the mammalian biosynthesis of leukotriene $B_4$, as well as leukotrienes $C_4$, $D_4$, $E_4$ and $F_4$, the active elements of the slow reacting substance of anaphylaxis (SRS-A). The compounds of Formula I are thought to act as inhibitors of the mammalian 5-lipoxygenase enzyme system of the arachidonic acid cascade. This inhibition of the mammalian biosynthesis of leukotrienes indicates that the compositions are useful to treat, prevent or ameliorate, in mammals and especially in humans (1) pulmonary conditions including diseases such as asthma, (2) allergies and allergic reactions such as allergic rhinitis, contact dermatitis, allergic conjunctivitis and the like (3) inflammation such as arthritis, (4) pain, (5) skin conditions such as psoriasis and the like, and (6) cardiovascular conditions such as angina and the like, and that the compounds are cytoprotective agents.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemia; noxious agent induced damage or necrosis of hepatic, pancreatic, renal, or myocardial tissue, liver parenchymal damage caused by hepatoxic agents such as $CCl_4$ and D-galactosamine; ischemic renal failure; disease-induced hepatic damage, bile salt induced pancreatic or gastric damage; trauma- or stress-induced cell damage; and glycerol-induced renal failure.

The cytoprotective activity of a compound may be observed in both animal and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay.

A. Ethanol-Induced Gastric Ulcer Assay

Twenty-four hour fasted Sprague-Dawley (S.D.) rats are perorally (p.o.) does with 1.0 ml absolute ethanol. Fifteen to thirty minutes prior to ethanol administration, groups of rats each receive either an aqueous vehicle (aqueous methylcellulose 5% wt.) or the test compound at various doses perorally. One hour later, the animals are sacrificed and stomach mucosa are examined for resulting lesions.

B. Indomethacin-Induced Ulcer Assay

Indomethacin, 10 mg/kg p.o., is used to induce ulcers in 24 hour fasted S. K. rats. Fifteen minutes prior to indomethacin administration, groups of rats each receive either an aqueous vehicle (5% by weight methylcellulose) or the test compound at various doses perorally. Four hours later the animals are sacrifices and stomach mucosa are examined for resulting ulcers.

The magnitude of a prophylactic or therapeutic dose of a compound of Formula I will, of course, vary with the nature of the severity of the condition to be treated and with the particular compound of Formula I and its route of administration. When a compound of Formula I is used in a pharmaceutical composition, the effective concentration in the composition will vary as required by the mode of administration, dosage form and pharmocological effect and level desired. In general, the daily dose range for anti-asthmatic, anti-allergic or anti-inflammatory use and, generally, uses other than cytoprotection lies within the range of from about 0.01 mg to about 100 mg per kg body weight of a mammal. This dosage may be administered in a single or divided individual doses. More or less of the general daily dosage may be necessary depending upon the individual needs of the patient.

The exact amount of a compound of the Formula I to be used as a cytoprotective agent will depend on, inter alia, whether it is being administered to heal damaged cells or to avoid future damage, on the nature of the damaged cells or to avoid future damage, on the nature of the damaged cells (e.g., gastro-intestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID (for example, in a combination dosage form). Preferably it is administered prior to or simultaneously with the NSAID.

The effective daily dosage level for compounds of Formula I inducing cytoprotection in mammals, especially humans, will generally range from about 0.002 mg/kg to about 100 mg/kg, preferably from about 0.02 mg/kg to about 30 mg/kg. The dosage may be administered in single or divided doses.

Any suitable route of administration may be employed for providing a mammal, especially a human, with an effective dosage of a leukotriene antagonist. For example, oral, rectal, transdermal, parenteral, intramuscular, intravenous and the like may be employed. Dosage forms include tablets, troches, dispersions, suspensions, solutions, capsules and the like.

For treating pulmonary conditions such as asthma, the mode of administration may be oral, parenteral, by inhalation, by suppository and the like. Suitable oral dosage forms are tablets, elixirs, emulsions, solutions, capsules, including delayed or sustained release capsules and the like. Parenteral dosage forms include solutions, emulsions and the like. Dosage forms for administration by inhalation including sprays, aerosols and the like. These inhalation formulations may be administered in metered doses ranging from about 0.1 $\mu$g to about 200 $\mu$g, administered as needed.

For treating allergies or allergic reactions, such as allergic conjunctivitis, allergic rhinitis and the like, the Formula I compound may be administered by any conventional mode, e.g., orally, parenterally, topically, subcutaneously, by inhalation and the like. The oral and parenteral dosage forms are the same type as for the pulmonary treatment. The topical application dosage forms include ointments, salves, controlled release patches, emulsions, solutions, thixotropic formulations, powders, sprays and the like. For topical application, the percent by weight active ingredient (Formula I compound) may vary from about 0.001 to about 10%.

For treating inflammation the mode of administration may be oral, parenteral, by suppository and the like. The various dosage forms are the same as those described above.

For treating skin diseases such as psoriasis, atopic dermatitis and the like, oral, topical or parenteral administration is useful. For topical application to the diseased area salves, patches, controlled release patches, emulsions, etc., 1 are convenient dosage forms.

For use as an analgesic, i.e., for treating pain, any suitable mode of administration may be used, e.g., oral, parenteral, by insufflation, by suppository and the like.

For treating cardiovascular conditions such as angina pectoris, etc., any suitable mode of administration, e.g. oral, parenteral, topical, insufflation, etc. and dosage form e.g. pills, liquid formulations, controlled release capsules, controlled release skin patches, etc. may be used.

The compositions include compositions suitable for oral, rectal, ophthalmic, pummonary, nasal, dermal, topical or parenteral (including subcutaneous, intramuscular and intravenous) administration, although the most suitable route in any given case will depend on the nature an severity of the conditions being treated and on the nature of the active ingredient. They may be conveniently presented in unit dosage form and prepared by any of the methods well-known in the art of pharmacy.

For use where a composition for intravenous administration is employed, a suitable dosage range for anti-asthmatic, anti-inflammatory or anti-allergic use and, generally, uses other than cytoprotection is from about 0.01 mg to about 20 mg (preferably from about 0.1 mg to about 10 mg) of a compound of Formula I per kg of body weight per day and for cytoprotective use from about 0.002 mg to about 100 mg (preferably from about 0.02 mg to about 30 mg and more preferably from about 0.1 mg to about 10 mg) of a compound of Formula I of body weight per day. In the case where an oral composition is employed, a suitable dosage range for anti-asthmatic, anti-inflammatory or anti-allergic use and, generally, uses other than cytoprotection is from about 1 to about 100 of a compound of Formula I per kg of body weight per day, preferably from about 5 mg to about 40 mg per kg and for cytoprotective use from about 0.01 mg to about 100 mg (preferably from about 0.1 mg to about 30 mg and more preferably from about 0.1 mg to about 10 mg) of a compound of Formula I per kg of body weight per day.

For administration by inhalation, the compounds of the present invention are conveniently delivered in the form of an aerosol spray presentation from pressurized packs or a nebuliser. The preferred composition form inhalation is a powder which may be formulated as a cartridge from which the powder composition may be inhaled with the aid of a suitable device. In the case of a pressurized aerosol, the dosage unit may be determined by providing a valve to deliver a metered amount.

In practical use, leukotriene antagonists of Formula I can be combined as the active ingredient in intimate admixture with a pharmaceutical carrier according to conventional pharmaceutical compounding techniques and using conventional ingredients, e.g. diluents, carriers, etc. The carrier may take a wide variety of forms depending on the form of preparation desired form administration, e.g., oral or intravenous. In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations such as, for example, powders, capsules and tablets and capsules represent the most advantageous oral dosage unit form, in which case solid pharmaceutical carriers are obviously employed. If desired, tablets may be sugar coated or enteric coated by standard techniques.

In addition to the common dosage forms set above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are incorporated herein by reference.

Dosage forms for application to treat the eye are disclosed in U.S. Pat. No. 4,348,398, the disclosure of which is incorporated herein by reference.

Pharmaceutical compositions of the present invention suitable for oral administration and by inhalation in the case of asthma therapy may be presented as discrete units such as capsules, cachets or tablets each containing an predetermined amount of the active ingredient, as a powder or granules or as a solution or suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Molded tablets may be made by molding in a suitable machine, a mixture of the powdered compound moistened with an inert liquid diluent. Desirably, each tablet contains from about 25 mg to about 500 mg of the active ingredient and each cachet or capsule contains from about 25 to about 500 mg of the active ingredient.

The following are examples of representative pharmaceutical dosage forms:

| Injectible Suspension | mg/mL |
| --- | --- |
| Compound of Formula I | 2 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Aerosol for Oral Inhibition | mg/can (200 doses/can) |
| --- | --- |
| Compound of Formula I | 2–40 |
| Oleic Acid | 0.2–4.0 |
| Trichloromonofluoro methane | 5,000–8,000* |
| Dichloromonofluoro methane | 15,000–12,400* |
| *To a total of 20,400 | |

| Cream | mg/g |
| --- | --- |
| Compound of Formula I | 1–100 |
| Cetyl alcohol | 130.0 |
| Sodium Lauryl Sulfate | 15.0 |
| Propylene Glycol | 100.0 |
| Benzalkonium chloride | 1.5 |
| Purified Water of sufficient quantity to make total 1 g | |

| Ointment | mg/g |
| --- | --- |
| Compound of Formula I | 1–100 |
| Benzalkonium chloride | 1.5 |
| Petrolatum of sufficient quantity to make total 1 g | |

| Tablet | mg/tablet |
| --- | --- |
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
| --- | --- |
| Compound of Formula I | 25 |
| Lactose Powder | 573.5 |
| Magnesium Stearate | 1.5 |
| | 600 |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

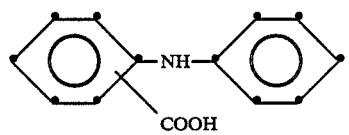

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

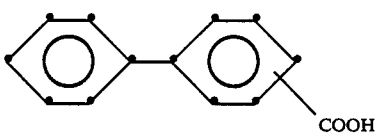

which can bear a variety of substituents and in which the free —COOH group can be in the form of a pharmaceutically acceptable salt group, e.g., —COO⁻Na⁺.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

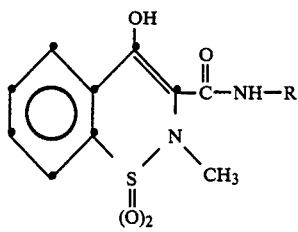

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid and ufenamate.

The following NSAIDs, designated by company code number (see e.g., Pharmaprojects), may also be used:

480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDS are acetyl salicylic acid, diclofenac, fenbufen, fenoprofen, flurbiprofen, ibuprofen, ketoprofen, naproxen, phenylbutazone, piroxicam, sulindac and tolmetin.

Pharmaceutical compositions comprising the Formula I compounds may also contain inhibitors of the biosynthesis of the leukotrienes such as are disclosed in EP No. 138,481 (Apr. 24, 1985), EP No. 115,394 (Aug. 8, 1984), EP No. 136,893 (Apr. 10, 1985), and EP No. 140,709 (May 8, 1985), which are hereby incorporated herein by reference.

The compounds of the Formula I may also be used in combination with leukotriene antagonists such as those disclosed in EP No. 106,565 (Apr. 25, 1984) and EP No. 104,885 (Apr. 4, 1984) which are hereby incorporated herein by reference and others known in the art such as those disclosed in EP Application Nos. 56,172 (July 21, 1982) and 61,800 (June 10, 1982); and in U.K. patent specification No. 2,058,785 (Apr. 15, 1981), which are hereby incorporated herein by reference.

Pharmaceutical compositions comprising the Formula I compounds may also contain as the second active ingredient, prostaglandin antgonists such as those disclosed in EP No. 11,067 (May 28, 1980) or thromboxane antagonists such as those disclosed in U.S. Pat. No. 4,237,160. They may also contain histidine decarboxylase inhibitors such as α-fluoromethyl histidine, described in U.S. Pat. No. 4,325,961. The compounds of the Formula I may also be advantageously combined with an $H_1$ or $H_2$-receptor antagonist, such as for instance benadryl, framamine, histadyl, phenergan, terfenadine, acetamazole, cimetidine, ranitidine, famotidine, aminothiadiazoles disclosed in EP No. 40,696 (Dec. 2, 1981) and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British patent specification Nos. 1,144,905 and 1,144,906. Another useful pharmaceutical composition comprises the Formula I compounds in combination with serotonin antagonists such as methysergide, the serotonin antagonists described in Nature, Vol. 316, pages 126–131, 1985, and the like. Each of the references referred to in this paragraph is hereby incorporated herein by reference.

The invention is further defined by reference to the following examples, which are intended to be illustrative and not limiting.

Preparation of Intermediates

PREPARATION 1

Ethyl 5,6-dichloro-3-methyl-4,7-benzofurandione-2-carboxylate

Ethyl 3-methyl-4,7-benzofurandione-2-carboxylate (0.5 g, 2 mmol) (from Preparation 25) was dissolved in acetic acid (75 mL) and $Cl_2$ gas was bubbled in for 30 min. The reaction mixture was poured into $H_2O$ and the precipitate formed was filtered. Purification by re-crystallization gave the title product, mp 174°–175° C.

'HNMR (CDCl₃) δ: 1.4 (3H,t),2.55 (3H,s), 4.4(2H,q)

PREPARATION 2

Ethyl 3,5,6-trimethyl-4,7-benzofurandione-2-carboxylate

Step 1. Ethyl 3-oxo-2-(3,4 dimethyl-2-methoxyphenoxy) butanoate

To a stirred solution of 3,4-dimethyl-2-methoxyphenol (101 g, 0.5 mole) in toluene (100 mL), cooled to 0° C., was added potassium hexamethyldisilazane (1.08 L, 0.675M in toluene). The solution was warmed to 80° C. over a period of 1 h. The reaction was treated with ethyl 2-chloroacetoacetate (101 mL, 0.55 mole) and then heated to reflux for 3 h. The reaction was cooled to RT and quenched with 25% NH₄OAc, and the products were extracted using EtOAc. Drying (Na₂SO₄) and evaporation of the solvent left a liquid which was fractionally distilled under vacuum (0.1 Torr) to give 3,4-dimethyl-2-methoxytrimethylsilyloxy benzene (bp 55°-100° C.) and 104 g of the title compound (bp 115°-6° C.)

Step 2. Ethyl 7-methoxy-3,5,6-trimethylbenzofuran-2-carboxylate

The material from Step 1 was cyclized to give the title compound using the method described by Royer* and Bisogne. Starting with 104 g of ketoester, the title compound was obtained.
* Bull. Soc. Chim. Fr. 521, (1969)

'HNMR (CDCl₃) δ=1.40 (3H, t, J=7.5 Hz), 2.27 (3H, s) 2.34 (3H,s), 2.52 (3H, s) 4.15 (3H, s) 4.42 (2H, q, J=7.5 Hz), 7.07 (1H, s)

Step 3. Ethyl 7-hydroxy-3,5,6-trimethylbenzofuran-2-carboxylate

To a solution of ethyl 7-methoxy-3,5,6-trimethylbenzofuran-2-carboxylate (97.2 g, 0.37 mole) (from Step 2) in dichloromethane (1 L) cooled to −78° C., was added a solution of BBr₃ (1.1 L, 1 M in dichloromethane). The reaction was warmed to −5° C. for and left for 15 mins. Quenching with 25% NH₄OAc buffer, extraction with EtOAc and drying (Na₂SO₄), followed by removal of solvent, afforded the product which was used as such for the following step.

'HNMR (CDCl₃) δ: 1.40 (3H, t, J=7.5 Hz) 2.27 (3H, s) 2.33 (3H, s), 2.50 (3H, s), 4.42 (2H, q, J=7.5 Hz) 5.53 (1H broad s, OH), 6.95 (1H, s)

Step 4. Ethyl 3,5,6-trimethyl-4,7-benzofurandione-2-carboxylate

The same procedure used to oxidize the phenol to the corresponding quinone in Preparation 3, Step 5 was employed to give the title compound from the compound of Step 3, mp 95°-96.5° C.

Analysis Calc'd: C, 64.12; H, 5.38; Found: C, 64.22; H, 5.41.

PREPARATION 3

2-(4-methoxybenzyl)-3,5,6-trimethyl-4,7-benzofurandione

Step 1. 7-hydroxy-3,5,6-trimethylbenzofuran-2-carboxylic acid

Ethyl 7-hydroxy-3,5,6-trimethylbenzofuran-2-carboxylate (90 g, 0.37 mole) (from Preparation 2, Step 3) was dissolved in 1:1 MeOH/THF (600 mL) and cooled to 0° C. Dropwise addition of 2N NaOH (750 mL) followed by warming to room temperature for a 2 hr period effected saponification of the ester. The reaction was acidified with conc. HCl (150 mL) and the product extracted into EtOAc, dried (Na₂SO₄) and the solvent evaporated to give the carboxylic acid used directly in the next step.

Step 2. 7-Hydroxy-3,5,6-trimethylbenzofuran

The carboxylic acid from Step 1 (80 g, 0.37 mole) was dissolved in quinoline (750 mL) and Cu powder (16 g) was added to the solution. The reaction was heated to reflux for 90 min, cooled and 6N HCl (2L) was added. Extraction with EtOAc followed by chromatography on silica gel produced the title compound.

'HNMR (CDCl₃) δ: 2.22 (3H, d, J=1.5 Hz) 2.29 (3H, s) 2.37 (3H, s), 5.34 (1H, s, OH) 6.92 (1H, s), 7.32 (1H, q, J=1.5 Hz)

Step 3. 7-hydroxy-2-(4-methoxybenzoyl)-3,5,6-trimethylbenzofuran

To p-anisoyl chloride (205 g) in 1,2-dichloroethane (2 L), cooled to 0° C., was added AlCl₃ (240 g). The reaction mixture was warmed to room temperature and a solution of 7-hydroxy-3,5,6-trimethylbenzofuran (51 g) in 1,2-dichloroethane (400 mL) was added dropwise. The reaction was stirred for 5½h then quenched with H₂O (2 L). The organic layer was separated and the aqueous layer was extracted with CH₂Cl₂. The combined extracts were washed with 25% NH₄OAc buffer, dried (Na₂SO₄) and filtered on silica gel to give 170 g of crude material which was used as such in the next step.

Step 4. 7-Hydroxy-2-(4-methoxybenzyl)-3,5,6-trimethylbenzofuran

The crude material from Step 3 was dissolved in ethylene glycol (600 mL) and KOH pellets (125 g) and anhydrous hydrazine (36 mL) were added. The reaction was heated to 150° C. for 2 hr, then cooled to RT (room temperature) and diluted with 10% NH₄OAc buffer (1.5 L) and the product was extracted into EtOAc. The crude product was chromatographed on silica gel (5% EtOAc/toluene) to yield the title compound, which was recrystallized in ether/hexane.

'HNMR (CDCl₃) δ: 2.17 (3H, s), 2.25 (3H, s), 2.34 (3H, s), 3.78 (3H, s), 4.01 (2H, s), 5.19 (1H, s, OH), 6.82 (2H, d, J=8Hz), 6.84 (1H, s), 7.13 (2H, d, J=8Hz)

Step 5. 2-(4-Methoxybenzyl)-3,5,6-trimethyl-4,7-benzofurandione

A solution of 7-hydroxy-2-(-4-methoxybenzyl)-3,5,6-trimethylbenzofuran from Step 4 (8.6g, 29 mmol) in acetone (1.5 L) was added rapidly to a solution of potassium nitrosodisulfonate (Fremy's salt) (25 g, 93 mmol) in 0.055 M KH₂PO₄ buffer (1.5 L) at room temperature. The reaction was slowly heated to 45° C. over a period of 2 hr. The reaction was then cooled and the quinone was extracted with EtOAc (2×, 500 mL). Evaporation of the organic solvent gave a solid residue which was crystallized and re-crystallized from EtOH, to give the title compound, mp 111°-113° C.

Calc'd for C₁₈H₁₈O₃: C 73.53; H 5.84; Found: C 73.54; H 5.84.

PREPARATION 4

Ethyl 6-methoxy-3-methyl-5-propyl-4,7-benzofurandione-2-carboxylate

Ethyl 4-hydroxy-6-methoxy-3-methylbenzofuran-2-carboxylate (7.1 mmol) was treated with $K_2CO_3$ (10.6 mmol) and allyl bromide (10.6 mmol) and heated in methyl ethyl ketone (50 mL) for 1 h. The reaction was extracted into $Et_2O$ and washed with 1% HCl, to give the allyl ether after drying and evaporation of the solvent.

The allyl ether was heated to reflux in O-dichlorobenzene for 40 min, and the rearranged 5-allyl product was purified by flash chromatography.

Hydrogenation with Pd-C catalyst (100 mg) in EtOH at 25–30 psi $H_2$ for 30 min followed by Fremy salt oxidation as in Preparation 3, Step 5 gave the title compound, mp 69°–70° C.

'HNMR ($CDCl_3$) δ: 0.95 (3H, t), 1.3–1.7 (5H, complex m) 1.50 (2H, dd), 1.60 (3H, s), 4.04 (3H, s), 4.38 (2H, q)

PREPARATION 5

Ethyl 6-chloro-3-methyl-5-propyl-4,7-benzofurandione-2-carboxylate

Following the procedure of Preparation 9, but starting with ethyl 3-methyl-5-propyl-4,7-benzofuran-dione-2-carboxylate (from Preparation 26), the title compound was obtained, mp 91.5°–93° C.

'HNMR (acetone-d6) δ: 0.98 (3H, t), 2.39 (3H, t), 1.50 (2H, Sextet), 2.60 (3H, s), 2.70 (2H, dd), 4.39 (3H, q)

PREPARATION 6

Ethyl 3-methyl-5-propyl-6-ethylthio-4,7-benzofurandione-2-carboxylate

Following the procedure Preparation 11 but starting with ethyl 3-methyl-5-propyl-4,7-benzofurandione-2-carboxylate (from Preparation 26) the title compound was prepared, m.p. 100°–101° C.

Analysis Calc'd: C, 60.70; H, 5.99; S, 9.53; Found: C, 60.43; H, 6.13; S, 10.09.

PREPARATION 7

Ethyl 3-methyl-5-propyl-6-ethylsulfinyl-4,7-benzofurandione-2-carboxylate

Following the procedure of Preparation 12 but starting with the product of Preparation 6, the title compound was prepared, mp 137°–138° C.

Analysis calc'd: C, 57.94; H, 5.72; S, 9.10; Found: C, 58.27; H, 5.69; S, 10.29.

PREPARATION 8

Ethyl 3-methyl-5-propyl-6-ethylsulfonyl-4,7-benzofurandione-2-carboxylate

Following the procedure for Preparation 13, but starting with the product of Preparation 6, the title compound was prepared, mp 128°–129° C.

Analysis calc'd: C, 65.98; H, 6.04; S, 8.01; Found: C, 65,89; H, 5.92; S, 8.51.

PREPARATION 9

2-(3-Chloro-4-methoxybenzyl)-6-chloro-3-methyl-5-propyl-4,7-benzofurandione

A solution of 2-(4-methoxybenzyl)-3-methyl-5-propyl-4,7-benzofurandione (from Preparation 28) (0.5 g) in AcOH (10 mL) was saturated with gaseous $Cl_2$ for 5 minutes. Chromotagrophy on silica gel afforded the title compound, mp 134.5°–136° C.

'HNMR ($CDCl_3$) δ: 1.01 (3H, t), 1.4–1.6 (2H, sextet), 2.29 (3H, s), 2.68 (2H, dd), 3.90 (3H, s), 4.00 (2H, s), 6.86 (1H, d), 7.11 (1H, dd), 7.20 (1H, d)

PREPARATION 10

3,6-Dimethyl-2-(4-methoxybenzyl)-5-propyl-4,7-benzofurandione

A solution of 2-(4-methoxybenzyl)-3-methyl-5-propyl-4,7-benzofurandione (from Preparation 28) (0.36 g, 1.1 mmol) is EtOAc (50 mL) was stirred over an aqueous solution of $Na_2S_2O_4$ (sat'd) for 16 hours. The EtOAc layer was separated, dried ($MgSO_4$) and the solvent removed to give a solid residue. This residue was dissolved in 1,2-dichloroethane (10 mL) and N,N-dimethylmethylene-ammonium iodide (725 mg) was added.

The reaction was heated to 60° C. for 3 h, then EtOH (10 mL) was added followed by $NaBH_4$ (0.4 g). The reaction was heated to reflux for 20 min. Saturated $NH_4Cl$ was added and the product was extracted with $Et_2O$ to give the title compound, mp 114°–114.5° C.

Analysis Calc'd: C, 74.54; H, 6.55; Found: C, 74.22; H, 6.30.

PREPARATION 11

2-(4-methoxybenzyl)-3-methyl-5-propyl-6-ethylthio-4,7-benzofurandione

To a suspension of 2-(4-methoxybenzyl)-3-methyl-5-propyl-4,7-benzofurandione (from Preparation 28) (0.988 g, 3.05 mmol) in MeOH (23 mL) was added ethanethiol (2.5 mL). After a few minutes, the yellow quinone passed into solution giving a reddish colour. The reaction was cooled to 0° C. and solid $FeCl_3$ (2.5g) was added. The reaction was quenched 10% HCl and extraction with $CH_2Cl_2$ afforded the crude product which was chromatographed on silica gel (5% EtOAc/hexane) to yield the title compound.

Analysis Calc'd: C, 68.72; H, 6.29; S, 8.34; Found: C, 68.44; H, 6.09; S, 9.02.

PREPARATION 12

2-(4-methoxybenzyl)-3-methyl-5-propyl-6-ethylsulfinyl-4,7-benzofurandione

To a solution of the product of Preparation 11 (247 mg, 0.66 mmol) in $CH_2Cl_2$ (30 mL) was added m-chloroperbenzoic acid (140 mg). The reaction was complete in a few minutes, and was quenched with 10% $NaCO_3$. The organic layer was separated, dried ($Na_2SO_4$) and the crude product was chromatographed on silica gel (30% EtOAc/hexane) to give the title compound.

Analysis Calc'd: C, 65.98; H, 6.04; S, 8.01; Found: C, 65.89; H, 5.92; S, 8.51.

PREPARATION 13

2-(4-methoxybenzyl)-3-methyl-5-propyl-6-ethylsulfonyl-4,7-benzofurandione

To a solution of the product of Preparation 11 (259 mg, 0.67 mmol) in $CH_2Cl_2$ (25 mL) was added m-chloroperbenzoic acid (289 mg). After 5 h the reaction was completed. The reaction was worked up following the procedure of Preparation 12 to yield the title compound.

Analysis Calc'd: C, 63.44; H, 5.81; S, 7.70; Found: C, 63.19; H, 5.96; S, 8.35.

PREPARATION 14

6-Amino-2-(4-methoxybenzyl)-3-methyl-5-propyl-4,7-benzofurandione

To a solution of 2-(4-methoxybenzyl)-3-methyl-5-propyl-4,7-benzofurandione (from Preparation 28) (295 mg, 0.91 mmol) in MeOH (3 mL) were added $NH_4Cl$ (109 mg) and $NaN_3$ (130 mg). The mixture was heated to reflux for 4 hours and the solvent was then removed in vacuo. Water was added and the product was extracted into $CH_2Cl_2$ and chromatographed on silica gel (15% EtOAc/hexane) to give the title compound.

'HNMR ($CDCl_3$) δ: 0.96 (3H, t, J—7.1 Hz), 1.46 (2H, m), 2.24 (3H, s), 2.30 (2H, dd, J—6.7 and 7.8 Hz), 3.78 (3H, s), 3.97 (2H, s), 4.88 (2H, broad s), 6.83 (2H, d, J—9.0 Hz), 7.13 (2H, d, J=9.0 Hz).

PREPARATION 15

3,5-Dimethyl-2-(4-methoxybenzyl)-6-propyl-4,7-benzofurandione

Starting with 7-hydroxy-3-methyl benzofuran, the corresponding 7-hydroxy-3-methyl-6-propyl benzofuran was prepared using the procedure described in Preparation 4. The 2-(4-methoxybenzyl) compound was formed according to the procedure of Preparation 3 (Steps 3 and 4). Finally Fremy's salt oxidation according to Preparation 3, Step 5 gave 2-(4-methoxybenzyl)-3-methyl-6-propyl-4,7-benzofurandione.

Following the procedure of Preparation 10, but starting 2-(4-methoxybenzyl)-3-methyl-6-propyl-4,7-benzofurandione, the title compound was obtained, m.p. 60°-61° C.

Analysis Calc'd: C, 74.54; H, 6.55; Found: C, 74.57, H, 6.61.

PREPARATION 16

2-(4-hydroxybenzyl)-3,5,6-trimethyl-4,7-benzofurandione

Following the procedure of Preparation 2, Step 3, but starting with the product of Preparation 3, the title compound was obtained.

'HNMR ($CDCl_3$) δ: 2.00 (3H, s), 2.04 (3H, s), 2.23 (3H, s), 3.92 (2H, s), 5.7 (1H, bs, OH), 6.77 (2H, d), 7.02 (2H, d).

PREPARATION 17

2-Ethyl-3,5,6-trimethyl-4,7-benzofurandione

Following the procedure of Preparation 3, Steps 3–5, but using acetyl chloride in place of p-anisoyl chloride in Step 3, the title compound was obtained.

'HNMR ($CDCL_3$) δ: 1.25 (3H, t), 2.05 (3H, s), 2.11 (3H, s), 2.21 (3H, s), 2.72 (2H, q)

PREPARATION 18

2-(3,4-methylenedioxybenzyl)-3,5,6-trimethyl-4,7-benzofurandione

Following the procedure of Preparation 3, Steps 3–5, but using 3,4-methylenedioxybenzoyl chloride in place of p-anisoyl chloride in Step 3, the title compound is obtained.

PREPARATION 19

2-[2-(4-methoxyphenyl)ethyl]-3,5,6-trimethyl-4,7-benzofurandione

Following the procedure of Preparation 3, Steps 3–5, but using 4-methoxyphenylacetyl chloride in place of p-anisoyl chloride in Step 3, the title compound is obtained.

PREPARATION 20

2-[1-(4-methoxyphenyl)ethyl]-3,5,6-trimethyl-4,7-benzofurandione

To 7-hydroxy-2-(4-methoxybenzoyl)-3,5,6-trimethyl benzofuran (250 mg) (from Preparation 3, Step 3) in THF (6 mL) was added MeLi (1.6M/$Et_2O$, 0.84 ml). The reaction was quenched with 25% $NH_4OAc$ and the product was extracted with $Et_2O$. The tertiary alcohol was treated with $LiAlH_4$ (0.4 g) and $AlCl_3$ (0.35 g) in $Et_2O$ (20 mL). The reaction was complete in 15 min and Fremy's salt oxidation of the crude material according to Preparation 3, Step 5 provided the title compound.

'HNMR ($CDCl_3$) δ: 1.68 (3H, d), 2.04 (3H, s), 2.08 (3H, s), 2.17 (3H, s), 3.75 (3H, s), 4.23 (2H, q), 6.83 (2H, d), 7.17 (2H, d).

PREPARATION 21

2-Phenylthio-3,5,6-trimethyl-4,7-benzofurandione

Step 1. 4,7-Dimethoxy-3,5,6-trimethylbenzofuran

A solution of 3,5,6-trimethyl-4,7-benzofurandione obtained by Fremy salt oxidation of 7-hydroxy-3,5,6-trimethylbenzofuran (Preparation 3, Step 2) (2.5 g, 13 mmol) in EtOAc (100 mL) was stirred together with a saturated solution of $Na_2S_2O_4$ (100 mL) for 16 h. The organic layer was separated, collected and dried ($Na_2SO_4$), and evaporated to dryness leaving a solid white residue. The crude residue was added to a suspension of NaH (0.72 g, 30 mmol) in dry DMF (50 mL) and maintained at 0° C. Methyl iodide (9.2 g, 65 mmol) was added and the reaction was warmed to RT over a 2 h period. Addition of $Et_2O$ followed by thorough washing with $H_2O$ (5×) afforded an etherial solution of the title compound. The organic phase was dried ($MgSO_4$) and the ether was evaporated to give a residue which was chromatographed on silica gel (20% $CH_2Cl_2$/EtOAc) to give the title compound.

'HNMR ($CDCl_3$) δ: 2.48 (s, 3H, $CH_3$), 2.51 (s, 3H, $CH_3$), 2.59 (d, 3H, $CH_3$) 3.02 (s, 3H, $CH_3$), 3.27 (s, 3H, $OCH_3$, 6.50 (q, 1H, aromatic H).

Step 2. 4,7-Dimethoxy-2-phenylthio-3,5,6-trimethylbenzofuran

To a solution of 4,7-dimethoxy-3,5,6-trimethylbenzofuran from Step 1 (155 mg, 0.7 mmol) in n-$Bu_2O$ (1 mL) was added nBuLi (0.5 mL, 0.8 mmol, 1.6 M hexanes) at RT and the reaction was stirred for 2 h. Diphenyl disulfide 220 mg, 1 mmol was added and the reaction was stirred overnight. Addition of $Et_2O$ and washing (2×) $H_2O$ followed by drying ($Na_2SO_4$) and concentration gave a Bu$_2$O solution of the crude product, which was chromatographed on silica gel (5% EtOAc/hexane) to afford the title compound.

'HNMR (CDCl$_3$) δ: 2.26 (3H, s, CH$_3$), 2.27 (3H, s, CH$_3$), 2.49 (3H, s, CH$_3$), 3.82 (3H, s, OCH$_3$), 4.04 (3H, s, OCH$_3$), 7.1–7.3 (5H, m, aromatic).

Step 3.
2-Phenylthio-3,5,6-trimethyl-4,7-benzofurandione

A solution of 4,7-dimethoxy-2-phenylthio-3,5,6-trimethylbenzofuran from Step 2 (200 mg, 0.64 mmol) in CH$_2$Cl$_2$ (10 mL) was cooled to −78° C. and a BBr$_3$ solution (2.8 mL, 2.8 mmol, 1M CH$_2$Cl$_2$) was added dropwise. The reaction was slowly warmed to room temperature then quenched with 25% NH$_4$OAc. Extraction with EtOAc followed by addition of powdered FeCl$_3$ and flash chromatography on silica gel (10% EtOAc/hex) afforded the title compound.

Calc'd for C$_{17}$H$_{14}$O$_3$S: C, 68.43; H, 4.73; S, 10.75; Found: C, 68.65; H, 4.66; S, 11.23.

PREPARATION 22

Methyl (3,5,6-trimethyl-4,7-benzofurandion-2-yl)-thioacetate

Following the procedure of Preparation 21, Steps 2 and 3, but using dimethyl dithiodiacetate in place of diphenyldisulfide the title compound was obtained.

'HNMR (acetond-d$_6$) δ: 2.05 (3H, s), 2.06 (3H, s), 2.30 (3H, s), 3.57 (2H, s), 3.71 (3H, s).

PREPARATION 23

(3,5,6-Trimethyl-4,7-benzofurandion-2-yl)thioacetic acid

Following the procedure of Preparation 3, Step 1, but starting with the product of Preparation 22, the title compound was obtained.

'HNMR (acetone d$_6$) δ: 2.22 (3H, s), 2.24 (3H, s), 2.45 (3H, s), 3.58 (2H, s).

PREPARATION 24

2-phenyl-3,5,6-trimethyl-4,7-benzofurandione

Step 1.
2-phenyl-4,7-dimethoxy-3,5,6-trimethylbenzofuran

A solution of 4,7-dimethoxy-3,5,6-trimethylbenzofuran (from Preparation 21, Step 1) (1.98 g, 9.0 mmol) in n-Bu$_2$O (12 mL) was treated with n-BuLi (6.0 mL, 1.6 M/hexanes) at 25° C. to form the 2-lithio species. THF (10 mL) was added followed by CuBr-Me$_2$S (1.9 g), phenyl iodide (1.2 mL) and pyridine (20 mL). The reaction was heated to reflux for 6 h. Hydrolysis with 10% HCl and extraction with EtOAc, followed by chromatography on silica gel (20% C$_6$H$_6$/CCl$_4$) afforded the title compound.

'HNMR (C$_6$D$_6$) δ: 2.24 (3H, s), 2.26 (3H, s), 2.47 (3H, s), 3.79 (3H, s), 4.08 (3H, s), 7.33 (1H, t), 7.44 (2H, t), 7.77 (2H, d).

Step 2. 2-phenyl-3,5,6-trimethyl-4,7-benzofurandione

Following the procedure for Preparation 21, Step 3, but using the product of Preparation 24, Step 1, the title compound was prepared.

'HNMR (CDCl$_3$) δ: 2.03 (3H, s), 2.06 (3H, s), 2.49 (3H, s), 7.3–7.5 (3H, m, aromatic), 7.68 (2H, dd, aromatic).

The starting materials for some of the preparations are to be found in the following publications: W. B. Whalley, J. Chem. Soc. 3229–3235 (1951) Preparation 25;

European Patent Application No. 146, 243 (June 26, 1985) Preparation 26; and

European Patent Application No. 65, 810 (Dec. 27, 1985) Preparation 28.

PREPARATION 25

Ethyl 3-methyl-4,7-benzofurandione-2-carboxylate

A mixture of ethyl 4-hydroxy-3-methylbenzofuran-2-carboxylate (2.2 g; 10 mmoles), N,N'-Bis (salicylidene) ethylenediaminocobalt (II) hydrate (650 mg; 2 mmoles) and N,N-dimethylformamide (50 ml) was stirred for 18 hours as oxygen was gently bubbled through the mixture. The mixture was diluted with diethyl ether (200 ml) and filtered. The filtrate was washed with H$_2$O (50 ml) three times, dried over sodium sulfate, filtered and evaporated. Trituration with a small volume of diethyl ether and filtration yielded the title compound, physical data for which are shown in Table 5.

Following the above described procedures, the compounds of Table 4 were prepared. In Table 5 are shown the physical data for Preparations 25–31.

TABLE 4

Id

| Prep. No. | R$^1$ | Y$^1$ | Y$^2$ | R$^3$ |
|---|---|---|---|---|
| 25 | CO$_2$Et | — | — | H |
| 26 | CO$_2$Et | — | — | n-Pr |
| 27 | H | — | — | n-Pr |
| 28 | CH$_2$C$_6$H$_3$Y$^1$Y$^2$ | 4-OMe | H | n-Pr |
| 29 | CH$_2$C$_6$H$_3$Y$^1$Y$^2$ | 4-OH | H | n-Pr |
| 30 | CH$_2$C$_6$H$_3$Y$^1$Y$^2$ | 4-OMe | H | H |
| 31 | CH$_2$CO$_2$Et | — | — | n-Pr |

TABLE 5

| Prep. No. | m.p. (°C.) | ANALYSIS OR 'H—NMR |
|---|---|---|
| 25 | 105–107 | Analysis Calc'd: C, 61.53; H, 4.30 Found: C, 61.90; H, 4.03 |
| 26 | 63–66 | Analysis Calc'd: C, 65.20; H, 5.83 Found: C, 65.12; H, 5.82 |
| 27 | 72–74 | Analysis Calc'd: C, 70.57; H, 5.92 Found: C, 70.50; H, 5.57 |
| 28 | 84–86 | Analysis Calc'd: C, 74.05; H, 6.20 Found: C, 74.06; H, 6.34 |
| 29 | | 'H—NMR (CDCl$_3$) δ: 0.9 (3H, t), 1.4 (2H, m), 2.3 (3H, s), 2.4 (2H, t), 3.95 (2H, s), 6.5(1H, s), 6.8 (2H, d), 7.1 (2H, d) |
| 30 | 129–131 | |
| 31 | | Analysis Calc'd: C, 66.19; H, 6.29 Found: C, 65.58; H, 6.36 |

Example 1

4,7-diacetoxy-2-(4-methoxybenzyl)-3,5,6-trimethylbenzofuran

A solution of 2-(4-methoxybenzyl)-3,5,6-trimethyl-4,7-benzofurandione (from Preparation 3) (0.5 g) in EtOAc (50 mL) was stirred vigorously with a saturated aqueous solution of Na$_2$S$_2$O$_4$ (50 mL) at 25° C. for 16 h. The organic layer was separated, dried (MgSO$_4$) and the solvent evaporated to give a white solid. The solid was dissolved in pyridine (10 mL) containing at catalytic amount of 4-(dimethylamino)pyridine and 3 equivalents of Ac$_2$O were added.

After 1 h at room temperature the reaction was diluted with Et$_2$O and washed with H$_2$O (3×) and brine (1×). Drying (Na$_2$SO$_4$) and removal of solvent afforded a white solid which was re-crystallized from EtOH to give the title compound.

HNMR (CDCl$_3$) δ: 2.09 (3H, s), 2.12 (3H, s), 2.14 (3H, s), 2.38 (6H, s), 3.75 (3H, s), 3.95 (2H, s), 6.78 (2H, d), 7.07 (2H, d)

Following the procedure of Example 1, the following compounds of the invention are prepared (Table 6).

Other advantageous pharmaceutical compositions comprise the Formula I compounds in combination with anti-cholinergics such as ipratropium bromide, bronchodilators such as the beta agonist salutamol, metaproterneol, terbutaline, fenoterol and the like, and the anti-asthmatic drugs theophylline, choline theophyllinate and enprofylline, the calcium antagonists nifedipine, diltaizem, nitrendipine, verapamil, nimodipine, felodipine, etc. and the corticosteroids, hydrocortisone, methylprednisolone, betamethasone, dexamethasone, eclomethasone, and the like.

What is claimed is:

1. A compound which is: 4,7-diacetoxy-2-(4-methoxybenzyl)-3,5,6-trimethylbenzofuran.

* * * * *

TABLE 6

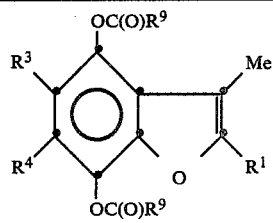

Ie

| Example | Starting Material Preparation | R$^1$ | Y$^1$ | Y$^2$ | R$^3$ | R$^4$ | R$^9$ |
|---|---|---|---|---|---|---|---|
| 2 | 9 | CH$_2$C$_6$H$_3$Y$^1$Y$^2$ | 3-Cl | 4-OMe | n-Pr | Cl | Me |
| 3 | 10 | CH$_2$C$_6$H$_3$Y$^1$Y$^2$ | 4-OMe | H | n-Pr | Me | Me |
| 4 | 11 | CH$_2$C$_6$H$_3$Y$^1$Y$^2$ | 4-OMe | H | n-Pr | SEt | Me |
| 5 | 12 | CH$_3$C$_6$H$_3$Y$^1$Y$^2$ | 4-OMe | H | n-Pr | S(O)Et | Me |
| 6 | 13 | CH$_2$C$_6$H$_3$Y$^1$Y$^2$ | 4-OMe | H | n-Pr | S(O)$_2$Et | Me |
| 7 | 15 | CH$_2$C$_6$H$_3$Y$^1$Y$^2$ | 4-OMe | H | Me | n-Pr | Me |
| 8 | 17 | Et | — | — | Me | Me | Me |
| 9 | 18 | CH$_2$C$_6$H$_3$Y$^1$Y$^2$ | 3,4-OCH$_2$O | — | Me | Me | Me |
| 10 | 19 | (CH$_2$)C$_6$H$_3$Y$^1$Y$^2$ | 4-OMe | H | Me | Me | Me |
| 11 | 20 | CH(CH$_3$)C$_6$H$_3$Y$^1$Y$^2$ | 4-OMe | H | Me | Me | Me |
| 12 | 21 | SC$_6$H$_3$Y$^1$Y$^2$ | H | H | Me | Me | Me |
| 13 | 22 | SCH$_2$CO$_2$Me | — | — | Me | Me | Me |
| 14 | 24 | C$_6$H$_3$Y$^1$Y$^2$ | H | H | Me | Me | Me |
| 15 | 16 | C$_6$H$_3$Y$^1$Y$^2$ | 4-OAc | H | Me | Me | Me |
| 16 | 3 | C$_6$H$_3$Y$^1$Y$^2$ | 4-OMe | H | Me | Me | t-Bu |
| 17 | 17 | Et | — | — | Me | Me | n-Pr |
| 18 | 3 | C$_6$H$_3$Y$^1$Y$^2$ | 4-OMe | H | Me | Me | H |